United States Patent [19]
Heijl et al.

[11] Patent Number: 5,598,235
[45] Date of Patent: Jan. 28, 1997

[54] METHOD AND AN APPARATUS FOR TESTING A SUBJECT'S RESPONSE TO VISUAL STIMULI

[76] Inventors: Anders Heijl, Danska vägen 62, S-226 39 Lund; Jonny Olsson, Fasanvägen 5A, S-227 31 Lund; Holger Rootzén, Olshögsvägen 6, S-223 60 Lund, all of Sweden

[21] Appl. No.: 408,033

[22] Filed: Mar. 21, 1995

[30] Foreign Application Priority Data

Mar. 22, 1994 [WO] WIPO ............... PCT/SE94/00256

[51] Int. Cl.$^6$ .................. A61B 3/02; A61B 3/00
[52] U.S. Cl. ............. 351/224; 351/237; 351/246
[58] Field of Search .................. 351/223, 222, 351/224, 226, 237, 243, 246

[56] References Cited

U.S. PATENT DOCUMENTS

| | | | |
|---|---|---|---|
| 4,334,738 | 6/1982 | Seckinger | 351/222 |
| 4,429,961 | 2/1984 | Sheingorn | 351/226 |
| 4,927,259 | 5/1990 | Weber | 351/224 |
| 5,080,478 | 1/1992 | O'Brien et al. | 351/224 |
| 5,381,195 | 1/1995 | Rootzen et al. | 351/222 |

FOREIGN PATENT DOCUMENTS

| | | |
|---|---|---|
| 0163674 | 12/1985 | European Pat. Off. . |
| 3135384 | 10/1983 | Germany . |
| 9220282 | 11/1992 | WIPO . |

*Primary Examiner*—Huy Mai

[57] ABSTRACT

In a method of testing a subject's response to visual stimuli, a plurality of visual stimuli are presented to the subject by means of a perimeter. After each stimulus presentation, the perimeter waits for a response from the test subject during at most a predetermined time period. The perimeter then classifies each stimulus as seen, unseen or uncertain, depending on whether a response is detected within the predetermined time period as well as on the time of receipt of any such detected response. Stimuli classified as uncertain are repeated and are not used for the calculation of threshold values.

16 Claims, 2 Drawing Sheets

METHOD AND AN APPARATUS FOR TESTING A SUBJECT'S RESPONSE TO VISUAL STIMULI

FIELD OF THE INVENTION

The present invention relates to visual testing, and in particular to an improved method and apparatus for testing a subject's response to visual stimuli.

BACKGROUND OF THE INVENTION

Perimetry is a very important and common test in clinical eye care, second only to the simple determination of visual acuity. It is used for examining the range and the sensitivity of a subject's visual field, e.g. in connection with diagnosis and treatment of glaucoma, for testing for neurological diseases, in mass screening etc.

In static threshold perimetry, the limit or threshold of a subject's light perception at a number of discrete locations in the visual field is determined. The test is conducted by means of a computerized perimeter, typically in the following way: the patient is seated in front of a perimeter and asked to look steadily at a centrally placed fixation target, e.g. on a screen or in a hemispherical bowl. Visual stimuli are presented successively with different intensities and at different locations. The patient is asked to press a response button every time he perceives a stimulus, whether close to or distant from the fixation target, whether faint or strong.

The test locations are usually tested in random order, a stimulus at a first test location being followed by a stimulus at another test location etc., and the next stimulus for the first test location being not presented until after several subsequent stimulus presentations.

After each presentation of a stimulus, the perimeter waits for a response during at most a predetermined time period. Stimuli which correspond to responses received within a predetermined response time window within the predetermined time period are classified as seen. Stimuli which correspond to responses received before and after the response time window are normally classified as unseen, as are stimuli for which no response at all is received. The response time window needs not to be the same for all test subjects. U.S. Pat. No. 5,381,195, by the inventors of the present application, discloses the use of a subject-adapted response time window.

However, it is well-known that patients sometimes press the button without having seen any stimulus at all, and they sometimes fail to press it despite having seen the stimulus. These kinds of responses are called false positive responses and false negative responses, respectively. It goes without saying that they affect the accuracy of the threshold determination.

The frequency of false positive responses may be examined by false positive catch trials. The perimeter then acts as when displaying a stimulus but without showing one, and registers whether the patient responds or not. The frequency of false negative responses may be examined by false negative catch trials. A strong, supraliminal stimulus is presented at a point where the threshold has already been measured, and the perimeter registers whether the patient responds or not. Often 20–30 catch trials are presented during a test.

There are different strategies for selecting test locations and intensities of the stimuli presented at these test locations in order to establish a patient's threshold for perception of light. In one common method, a stimulus is shown having an intensity close to an expected threshold value at each test location concerned. If the patient does not respond to the stimulus, the intensity of the subsequently presented stimuli is thereafter increased stepwise until a response is received from the patient, i.e. until a stimulus is seen. The first intensity level at which a response is received can be defined as the threshold of the test location concerned. The precision of the test can be increased by reversing the test process when the first response is received, and by continuing it in smaller steps with decreasing intensities until the first unseen stimulus is encountered. The threshold can then be defined as the average intensity level of the last seen stimulus and the first unseen stimulus. If, on the other hand, the patient responds to the first stimulus, the intensity is decreased stepwise until no response is received, whereupon the test procedure is reversed.

The above method of presenting series of visual stimuli with alternately increasing and decreasing intensities is called the staircase method.

In the staircase method, the intensity steps between stimuli of increasing/decreasing intensities are often constant, at least between reversals. A variant hereof is the Robbins-Monroe method where the steps between successive stimuli are gradually decreased.

Another method for determining threshold values is the Modified Binary Search (MOBS), according to which a stimulus with a selected intensity close to the expected threshold value of the subject is presented. If the stimulus is seen, its intensity value is regarded as the upper threshold boundary and, if it is not seen, as the lower threshold boundary. The intensity range is then divided into a series of increasingly smaller half-intervals until the upper and lower treshold boundaries are within a predefined range.

There are also other test strategies. However, they all classify each stimulus as either seen or unseen, using this classification as a basis for the selection of the next intensity of the test location and as a basis for determining the threshold value.

When the threshold values for all the test locations in the visual field have been determined, they are often compared with normal, previously determined threshold values for subjects of the same age to establish whether there are any deviations from normal, or with previous values for the same eye of the subject to establish whether a disease under observation has progressed or receded.

A problem in this context is that the measurement variations are considerable and that there is a high proportion of false positive and false negative answers. One reason for this may be that the test is very tiring. As described above, several stimuli of different intensities are presented at each test location on the screen. Since 50–100 test points are usually examined, one test consists of several hundred stimulus presentations. Typically, the time required for a complete static threshold perimetry test is about 10–20 minutes per eye.

The above-mentioned measurement variation makes it difficult to follow the development of a disease, because the errors of the calculated threshold values will be large. Furthermore, it makes it difficult to precisely define the limits between a normal visual field and an abnormal visual field. If the limits of what is considered as a normal visual field are too narrowly set, some patients will unnecessarily be further examined and/or treated. On the other hand, if the limits are too wide, the abnormal visual fields of some patients will be interpreted as normal, and these patients may not be further examined and/or treated.

One object of the present invention is, therefore, to provide a method and an apparatus which reduce the measurement variation and result in more precise threshold values.

SUMMARY OF THE INVENTION

The present invention introduces an additional class for the classification of the stimuli, namely the class of uncertain stimuli. Consequently, each stimulus is classified as seen, unseen or uncertain.

As mentioned above, the previously known perimeter waits for a response from the test subject during at most a predetermined time period. Stimuli which correspond to responses received within a predetermined response time window within the predetermined time period are classified as seen. Stimuli which correspond to responses received before and after the response time window are normally classified as unseen, as are stimuli for which no response at all is received.

According to the present invention, stimuli corresponding to responses received outside the response time window, and in particular responses received in a transitional time interval close to the beginning or the end thereof, are however classified as uncertain.

To increase the reliability of the test, stimuli classified as uncertain may be repeated and/or not used when calculating the threshold values. It appears that a false answer usually does more harm when calculating a threshold value than a lack of any information at all.

Stimuli may be reclassified during or after the test. To this end, the duration, the beginning and the end of the response time window and/or of the transitional time intervals may be adapted in accordance with the distribution of the times of reception of the responses.

The present invention is applicable in all visual tests where the patient is instructed to respond when perceiving a stimulus, and not to respond when not perceiving it. Examples of such tests other than perimerry are computerized, central or peripheral visual acuity testing, or determination of contrast sensitivity. In these kinds of tests, all stimuli may be presented in one location only, but the stimuli may have different appearances and each threshold value may be related to stimuli of a specific appearance.

The tests may be performed as screening tests, in which all presented stimuli may be of the same strength, or as threshold tests, in which visual stimuli of different strengths are presented to check or determine the threshold values of the subject under test. The strength of the stimuli is often the intensity of the stimuli, but may as well be the color, the size, the color saturation, the spatial frequency, the flicker frequency or any other parameter thereof which can be varied.

DESCRIPTION OF THE PREFERRED EMBODIMENT

Figure 1:
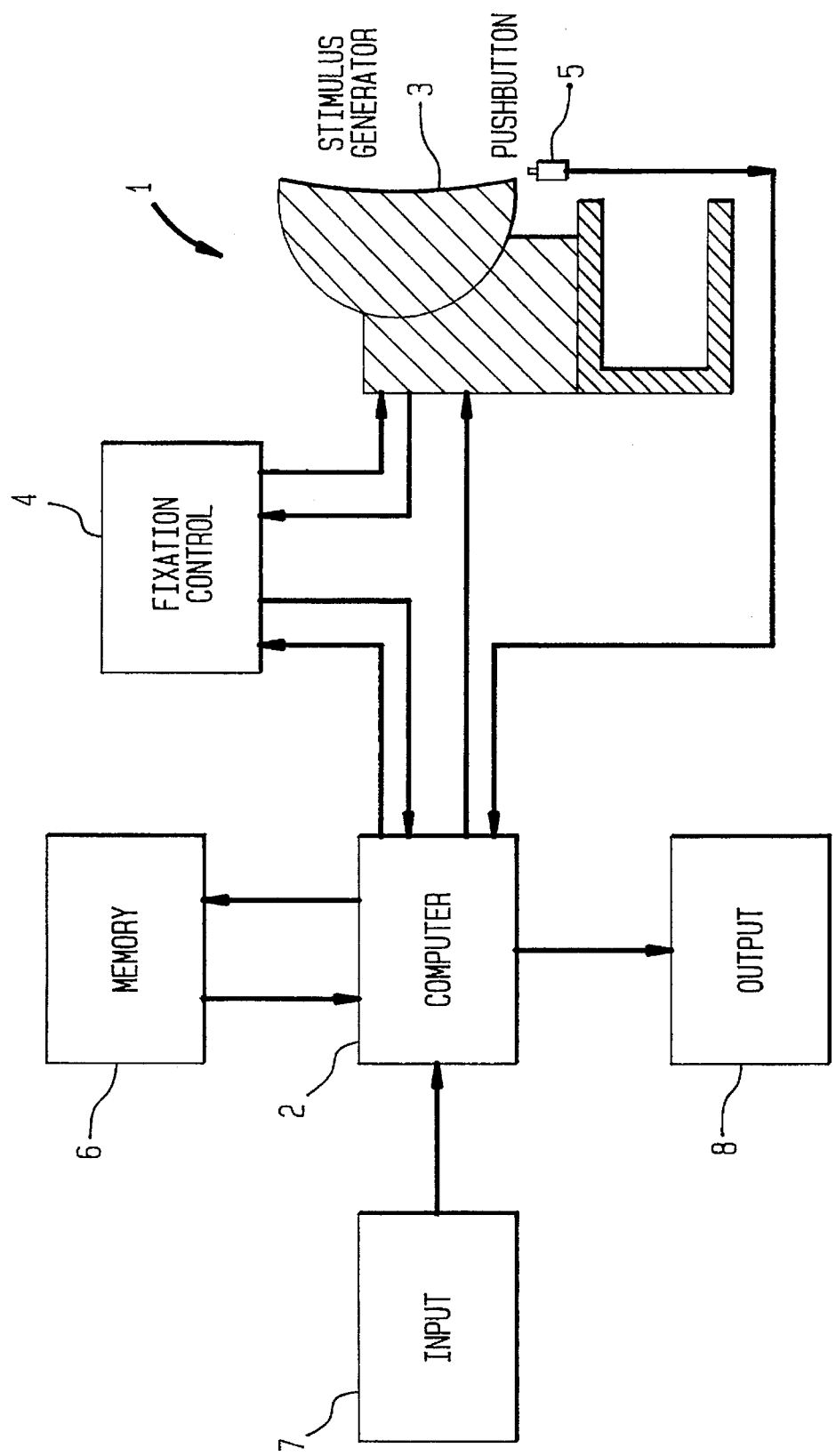
FIG. 1 schematically shows a computerized perimeter.

FIG. 1 shows schematically, partly in the form of a block diagram, the design of a computerized perimeter, by means of which the method of the invention can be carried out. The perimeter consists essentially of a stimulus generator 1 and a computer 2 for controlling the generator and for assessing the responses to presented stimuli that are received from the patient.

The stimulus generator 1 has a screen 3, which may be hemispherical or have some other suitable shape, and in front of which the patient is seated. The screen is provided with a fixation target, for example in the form of a light-emitting diode which is shining continuously and at which the patient is asked to look throughout the test. The stimulus generator 1 serves to provide well-defined visual stimuli at selected locations on the screen. These stimuli can be generated by means of a projection system or by means of fixed light sources (light-emitting diodes or optical fibres) or any other suitable means.

Advantageously, the perimeter also has means 4 for monitoring the patient's fixation of the fixation target, such that stimuli that are presented when the patient is blinking or does not maintain fixation can be sorted out or repeated. The fixation monitoring function may be implemented electronically or with the aid of a TV-camera. Other types of fixation monitoring are of course also possible.

The perimeter further comprises a press button 5, by means of which the patient should give a response each time he perceives a visual stimulus on the screen. Responses may also be obtained by measuring pupillary responses or visually evoked potentials or by any other suitable means. The press button 5 is connected to the computer 2 which assesses every response from the patient and, on the basis thereof, determines the location and the intensity of the next visual stimulus in compliance with a control program stored in the computer. The computer has a memory 6, in which for example the responses to the stimuli are stored. The computer is also provided with an input unit 7, by means of which an operator can supply information to the perimeter, and an output unit 8, by means of which the results of the visual field tests are presented. The input unit 7 may, for example, consist of a keyboard and the output unit 8 of a printer or a display device.

The physical design of the perimeter described above does not differ from that of prior-art perimeters. As will be explained hereinafter, the perimeter of the invention is however operated in a new manner.

Figure 2:
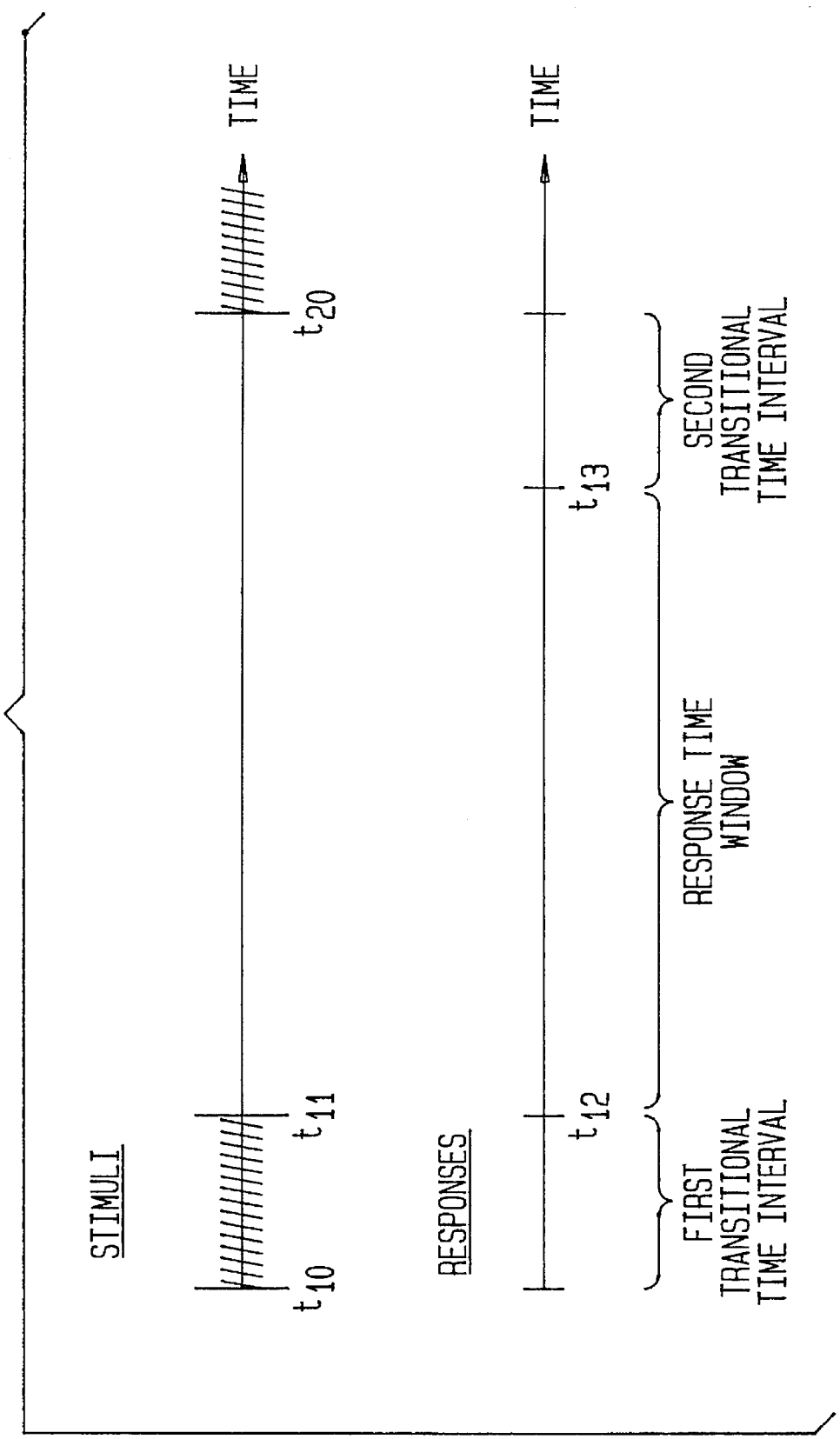
FIG. 2 is a time diagram showing the different time intervals used for the classification of a stimulus according to the present invention.

FIG. 2 schematically illustrates the progress of part of a visual field test according to the invention. At time t10, the presentation of a visual stimulus is started. It lasts to time t11. The interval t10–t11, i.e. the duration of the visual stimulus, normally is 200 ms. At time t12, which can be either during or after the presentation of the stimulus, a response time window starts. It lasts to time t13. The response time window may, for instance, start 200 ms from the onset of the visual stimulus, i.e. at the end of the stimulus presentation, and last 1800 ms. The presentation of the next stimulus is started either shortly after a response has been received or shortly after the end of the response time window, at time t20. The time t20 may, for instance, be 2200 ms after the onset of the first visual stimulus.

Since the reaction time varies considerably within a population, it is difficult to delimit the response time window t12–t13 so that all responses received inside the window represent stimuli actually seen and no response received outside the window represents a seen stimulus. To mitigate the effect of the sharp delimitation of the response time window, a first and a second transitional time interval are defined immediately before and immediately after the response time window, respectively. The transitional time intervals may, for instance, have a duration of about 100–300 ms, preferably about 200 ms. They need not be of the same duration. The first transitional time interval may last from the beginning of the presentation of the visual stimulus to the beginning of the time response window, and the second transitional time interval may last from the end of the response time window to the start of the presentation of the next stimulus. However, they may also be of shorter duration. In that case, stimuli received outside the response time window and the transitional time intervals may be ignored. In some applications, it may suffice to have only one transitional time interval.

During a test, the stimuli are classified as follows. If a response is received within the response time window, i.e. between t12 and t13, the corresponding stimulus is recorded as seen. If a response is received within the first or the second transitional time interval, between t11 and t12 or between t13 and t20, it is considered as uncertain and the corresponding stimulus is consequently classified as uncertain. If no response is received during the predetermined time period, the visual stimulus is recorded as unseen. Likewise, if a response is received within the predetermined time period but outside the response time window and the first and the second transitional time interval, the visual stimulus is classified as unseen.

If a response is received within the response time window, the perimeter does not wait for the remaining time of the response time window to elapse but begins the preparation for the next stimulus presentation. Any further responses received during the preparation for the next stimulus presentation are ignored.

According to U.S. Pat. No. 5,381,195, the limits of the response time window may be changed during and/or after the test in order to adjust the response time window to the recorded response times of a test subject. This subject-adapted response time window can be used for reclassifying the previously presented stimuli after the test. If the limits of the response time window are changed, the limits of the first and/or the second transitional time intervals may also be changed. As a result, stimuli previously classified as uncertain may be reclassified as seen or unseen. According to the present invention, the limits of the transitional time intervals may also be changed during and/or after the test, depending on the distribution of the response times of the test subject.

Thus, the embodiments of the present invention is a method of testing a subject's response to visual stimuli, which method comprises the steps of: (a) successively presenting a plurality of visual stimuli to the subject; (b) detecting any response received from the subject within a predetermined time period as a result of each presentation of a visual stimulus; and (c) classifying each presented stimulus as seen, unseen or uncertain depending on whether a response is detected within the predetermined time period as well as on the time of receipt of any such detected response. Further, in a first alternative of the one embodiment, the step of classifying comprises the substeps of: (c1) classifying a presented stimulus as seen, if a response is received within a predetermined response time window within the predetermined time period; (c2) classifying a presented stimulus as uncertain, if a response is received within a predetermined time intervals before the beginning or after the end of the predetermined response time window; and (c3) classifying a presented stimulus as unseen, if it is classified as neither seen nor uncertain. Further, in a specific example of the first alternative of the one embodiment, the predetermined time interval before the beginning of the predetermined response time window and the predetermined time interval after the end of the predetermined response time window each have a duration of approximately 100–300 ms. Futher, in a second alternative of the one embodiment, the step of classifying comprises of: (c1) classifying a presented stimulus as seen, if a response is received within a predetermined response time window within the predetermined time period; (c2) classifying a presented stimulus as uncertain, if a response is received within a predetermined time intervals before the beginning of the response time window and (c3) classifying a presented stimulus as unseen, if it is classified as neither seen nor uncertain. Further, in a specific example of the second alternative of the one embodiment, the predetermined time interval before the beginning of the predetermined response time window has a duration of approximately 100–300 ms. Futher, in a third alternative of the one embodiment, the step of classifying comprises the substeps of: (c1) classifying a presented stimulus as unseen, if no response is received within the predetermined time period; (c2) classifying a presented stimulus as seen, if a response is received within a predetermined response time window within the predetermined time period; and (c3) classifying a presented stimulus as uncertain, if it is classified as neither seen nor unseen. Futher, in a fourth alternative of the one embodiment, each presented stimulus has a selected strength and the method further comprises the step of repeating a presented stimulus which is classified as uncertain with the same strength. Further, in a fifth alternative of the one embodiment, each presented stimulus has a selected strength and is presented at one of a plurality of test locations, wherein the method further comprises the step of calculating a threshold value for the subject's perception of visual stimuli for each of the test locations, and wherein only those stimuli classified as seen or unseen are used for the threshold calculations.

A second embodiment of the present invention is a method of testing a subject's response to visual stimuli, comprising the steps of: (a) determining a preliminary response time window and at least one preliminary transitional time interval in connection with the preliminary response time window; (b) successively presenting a plurality of visual stimuli to the subject; (c) recording the time of reception of any response received from the subject within a predetermined time period from each presentation of a visual stimulus; (d) preliminarily classifying a presented stimulus as seen if a response was received within the preliminary response time window, preliminarily classifying a presented stimulus as uncertain if a response was received within said at least one preliminary transitional time interval, and preliminarily classifying a presented stimulus as unseen if it is classified as neither seen nor uncertain; (e) calculating a subject-adapted response time window, and at least one subject-adapted transitional time interval in connection with the subject-adapted response time window, on the basis of the recorded times of reception, and reclassifying the previously presented stimuli by means of the subject-adapted response time window and said at least one subject-adapted transitional time interval.

A third embodiment of the present invention is a method of testing a subject's response to visual stimuli, comprising the steps of: (a) determining a response time window and at least one preliminary transitional time interval in connection with the response time window; (b) successively presenting a plurality of visual stimuli to the subject; (c) recording the time of reception of any response received from the subject within a predetermined time period from each presentation of a visual stimulus; (d) preliminarily classifying a presented stimulus as seen if a response was received within the response time window, preliminarily classifying a presented stimulus as uncertain if a response was received within said at least one preliminary transitional time interval, and preliminarily classifying a presented stimulus as unseen if it is classified as neither seen nor uncertain; (e) calculating at least one subject-adapted transitional time interval in connection with the response time window, on the basis of the recorded times of reception, and reclassifying the previously presented stimuli by means of the response time window and said at least one transitional time interval.

A fourth embodiment of the present invention is a method of testing a subject's response to visual stimuli, comprising the steps of: (a) determining a preliminary response time window and at least one transitional time interval in connection with the preliminary response time window; (b) successively presenting a plurality of visual stimuli to the subject; (c) recording the time of reception of any response received from the subject within a predetermined time period from each presentation of a visual stimulus; (d) preliminarily classifying a presented stimulus as seen if a response was received within the preliminary response time window, classifying a presented stimulus as uncertain if a response was received within said at least one transitional time interval, and preliminary classifying a presented stimulus as unseen if it is classified as neither seen nor uncertain; (e) calculating a subject-adapted response time window, on the basis of the recorded times of reception, and reclassifying the previously presented stimuli by means of the subject-adapted response time window.

A fifth embodiment of the present invention is an apparatus for testing a subject's response to visual stimuli, comprising: (a) means for determining a response time window and at least one transitional time interval in connection with the response time window; (b) means for successively presenting a plurality of visual stimuli to the subject; (c) a memory recording the time of reception of any response received from the subject within a predetermined time period from each presentation of a visual stimulus; (d) means for preliminarily classifying a presented stimulus as seen if a response was received within the preliminary response time window, for preliminarily classifying a presented stimulus as uncertain if a response was received within said at least one transitional time interval, and for preliminary classifying a presented stimulus as unseen if it is classified as neither seen nor uncertain; (e) means for modifying the response time window and/or said at least one transitional time interval according to the recorded times of reception; and (f) means for reclassifying the previously presented stimuli by means of the modified response time window and/or transitional time interval.

What we claim and desire to secure by Letters Patent is:

1. A method of testing a subject's response to visual stimuli, comprising the steps of:

successively presenting a plurality of visual stimuli to the subject;

detecting any response received from the subject within a predetermined time period as a result of each presentation of a visual stimulus as well as the time of receipt of the detected response; and classifying each presented stimulus as one of the following: seen, unseen or uncertain;

wherein the step of classifying comprises the substeps of:
    classifying a presented stimulus as seen, if a response is received within a predetermined response time window within the predetermined time period;
    classifying a presented stimulus as uncertain, if a response is received within predetermined time interval before the beginning or after the end of the predetermined response time window; and
    classifying a presented stimulus as unseen, if it is classified as neither seen nor uncertain.

2. A method as set forth in claim 1, wherein the predetermined time interval before the beginning of the predetermined response time window and the predetermined time interval after the end of the predetermined response time window each have a duration of approximately 100–300 ms.

3. A method as set forth in claim 1, wherein each presented stimulus has a selected strength, and wherein the method further comprises a step of presenting again a presented stimulus which is classified as uncertain with the same strength.

4. A method as set forth in claim 1, wherein the step of successively presenting comprises, for each one of a plurality of test locations, presenting a visual stimulus to the subject at the one of the plurality of test locations, one or more times, each presentation of a visual stimulus having a selected strength, wherein the method further comprises the steps of calculating, for each one of the plurality of test locations, a threshold value for the subject's perception of visual stimuli using only those stimuli classified as seen or unseen.

5. A method of testing a subject's response to visual stimuli, comprising the steps of:

successively presenting a plurality of visual stimuli to the subject;

detecting, any response received from the subject within a predetermined time period as a result of each presentation of a visual stimulus as well as the time of receipt of the detected response; and classifying each presented stimulus as one of the following: seen, unseen or uncertain;

wherein the step of classifying comprises the sub steps of:
    classifying a presented stimulus as seen, if a response is received within a predetermined response time window within the predetermined time period;
    classifying a presented stimulus as uncertain, if a response is received within a predetermined time interval before the beginning of the predetermined response time window; and
    classifying a presented stimulus as unseen, if it is classified as neither seen nor uncertain.

6. A method as set forth in claim 5 wherein the predetermined time interval before the beginning of the predetermined response time window has a duration of approximately 100–300 ms.

7. A method as set forth in claim 5, wherein each presented stimulus has a selected strength, and wherein the method further comprises a step of presenting again a presented stimulus which is classified as uncertain with the same strength.

8. A method as set forth in claim 5, wherein the step of successively presenting comprises, for each one of a plurality of test locations, presenting a visual stimulus to the subject at the one of the plurality of test locations, one or more times, each presentation of a visual stimulus having a selected strength, wherein the method further comprises the steps of calculating, for each one of the plurality of test locations, a threshold value for the subject's perception of visual stimuli using only those stimuli classified as seen or unseen.

9. A method of testing a subject's response to visual stimuli, comprising the steps of:

successively presenting a plurality of visual stimuli to the subject;

detecting any response received from the subject within a predetermined time period as a result of each presentation of a visual stimulus as well as the time of receipt of the detected response; and classifying each presented stimulus as one of the following: seen, unseen or uncertain;

wherein the step of classifying comprises the substeps of;
classifying a presented stimulus as unseen, it no response is received within the predetermined time period;
classifying a presented stimulus as seen, if a response is received within a predetermined respond time window within the predetermined time period; and
classifying a presented stimulus as uncertain, if it is classified as neither seen nor unseen.

10. A method as set forth in claim 9, wherein each presented stimulus has a selected strength, and wherein the method further comprises a step of presenting again a presented stimulus which is classified as uncertain with the same strength.

11. A method as set forth in claim 9, wherein the step of successively presenting comprises, for each one of a plurality of test locations, presenting a visual stimulus to the subject at the one of the plurality of test locations, one or more times, each presentation of a visual stimulus having a selected strength, wherein the method further comprises the steps of calculating, for each one of the plurality of test locations, a threshold value for the subject's perception of visual stimuli using only those stimuli classified as seen or unseen.

12. A method of testing a subject's response to visual stimuli, comprising the steps of:
determining a preliminary response time window and at least one transitional time interval in connection with the preliminary response time window;
successively presenting a plurality of visual stimuli to the subject;
recording the time of reception of any response received from the subject within a predetermined time period which includes the preliminary response time window and the at least one transitional time interval from each presentation of a visual stimulus;
preliminarily classifying a presented stimulus as seen if a response was received within the preliminary response time window, classifying a presented stimulus as uncertain if a response was received within said at least one transitional time interval, and preliminarily classifying a presented stimulus as unseen if it is classified as neither seen nor uncertain;
calculating a subject-adapted response time window, on the basis of the recorded times of reception, and reclassifying the previously presented stimuli by means of the subject-adapted response time window.

13. An apparatus for testing a subject's response to visual stimuli, comprising:
means for successively presenting a plurality of visual stimuli to the subject;
means for detecting a response received from the subject within a predetermined time period from each presentation of a visual stimulus as well as the time of receipt of the detected response; and
classifying means for classifying each presented stimulus as seen if the response is detected within a predetermined response time window within the predetermined time period; for classifying each presented stimulus as uncertain, if the response is detected within a predetermined time interval before the beginning or after the end of the predetermined response time window; and for classifying each presented stimulus as unseen, if it is classified as neither seen nor uncertain.

14. An apparatus for testing a subject's response to visual stimuli, comprising:
means for determining a response time window and at least one transitional time interval in connection with the response time window;
means for successively presenting a plurality of visual stimuli to the subject;
a memory recording the time of reception of any response received from the subject within a predetermined time period which includes the response time window and at least one transitional time interval from each presentation of a visual stimulus;
means for preliminarily classifying a presented stimulus as seen if a response was received within the preliminary response time window, for preliminarily classifying a presented stimulus as uncertain if a response was received within said at least one transitional time interval, and for preliminarily classifying a presented stimulus as unseen if it is classified as neither seen nor uncertain;
means for modifying the response time window according to the recorded times of reception; and
means for reclassifying the previously presented stimuli by means of the modified response time window and the at least one transitional time interval.

15. An apparatus for testing a subject's response to visual stimuli, comprising:
means for successively presenting a plurality of visual stimuli to the subject;
means for detecting a response received from the subject within a predetermined time period from each presentation of a visual stimulus as well as the time of receipt of the detected response; and
classifying means for classifying each presented stimulus as seen if the response is detected within a predetermined response time window within the predetermined time period; for classifying each presented stimulus as uncertain, if the response is detected within a predetermined time interval before the beginning of the predetermined response time window; and for classifying each presented stimulus as unseen, if it is classified as neither seen nor uncertain.

16. An apparatus for testing a subject's response to visual stimuli, comprising:
means for successively presenting a plurality of visual stimuli to the subject;
means for detecting a response received from the subject within a predetermined time period for each presentation of a visual stimulus as well as the time of receipt of the detected response; and
classifying means for classifying each presented stimulus as unseen if no response is detected within the predetermined time period; for classifying each presented stimulus as seen if the response is detected within a predetermined response time window within the predetermined time period; and for classifying each presented stimulus as uncertain if it is classified as neither seen nor unseen.

* * * * *